United States Patent
Oliveira et al.

(10) Patent No.: US 11,047,014 B2
(45) Date of Patent: Jun. 29, 2021

(54) METHOD FOR HIGH-THROUGHPUT SCREENING OF TRANSGENIC PLANTS

(71) Applicants: E. I. DU PONT DE NEMOURS AND COMPANY, Wilmington, DE (US); PIONEER HI-BRED INTERNATIONAL, INC., Johnston, IA (US)

(72) Inventors: Igor Cunha De Oliveira, Sao Paulo (BR); Dennis O'Neill, Ankeny, IA (US); Andrew Slattery, Grimes, IA (US); Jijun Zou, Johnston, IA (US)

(73) Assignees: PIONEER HI-BRED INTERNATIONAL, INC.; E. I. DU PONT DE NEMOURS AND COMPANY

( * ) Notice: Subject to any disclaimer, the term of this patent is extended or adjusted under 35 U.S.C. 154(b) by 255 days.

(21) Appl. No.: 16/042,577

(22) Filed: Jul. 23, 2018

(65) Prior Publication Data

US 2018/0327868 A1 Nov. 15, 2018

Related U.S. Application Data

(63) Continuation of application No. 14/236,461, filed as application No. PCT/US2012/047858 on Jul. 23, 2012, now abandoned.

(60) Provisional application No. 61/514,052, filed on Aug. 2, 2011.

(51) Int. Cl.
| | |
|---|---|
| *C12Q 1/68* | (2018.01) |
| *C12Q 1/6895* | (2018.01) |
| *A01H 1/04* | (2006.01) |
| *C12N 15/82* | (2006.01) |

(52) U.S. Cl.
CPC .......... *C12Q 1/6895* (2013.01); *A01H 1/04* (2013.01); *C12N 15/8216* (2013.01); *C12N 15/8218* (2013.01); *C12Q 2600/13* (2013.01)

(58) Field of Classification Search
CPC .................................................. C12Q 1/6895
See application file for complete search history.

(56) References Cited

U.S. PATENT DOCUMENTS

| | | | |
|---|---|---|---|
| 2004/0172684 A1 | 9/2004 | Kovalic et al. | |
| 2008/0028482 A1* | 1/2008 | Beazley ............ | C12N 15/8275 800/265 |
| 2009/0089897 A1 | 4/2009 | Abbitt et al. | |
| 2009/0320160 A1 | 12/2009 | Zhongsen | |

OTHER PUBLICATIONS

Bako, A., Gell, G. and Balázs, E., 2011. Quantification of transgene expression in maize (*Zea mays* L.) throughout the vegetation period. Plant breeding, 130(1), pp. 41-45. Epub Aug. 2010. (Year: 2010).*

Farhoud, H.J., 2010. Development of PCR methods for detection and quantification of genetically modified maize (Doctoral Dissertation, Middle East Technical University). (Year: 2010).*

Holden, M.J., Levine, M., Scholdberg, T., Haynes, R.J. and Jenkins, G.R., 2010. The use of 35S and Tnos expression elements in the measurementof genetically engineered plant materials. Analytical and bioanalytical chemistry, 396(6), pp. 2175-2187. (Year: 2010).*

JRC European Commission, 2010. Event-specific Method for the Quantification of Maize Line MON88017 Using Real-time RCR. Joint Research Centre Institute for Health and Consumer protection Molecular Biology and Genomics Unit. (Year: 2010).*

Nolan, T., Hands, R.E. and Bustin, S.A., 2006. Quantification of mRNA using real-time RT-PCR. Nature protocols, 1(3), pp. 1559-1582. (Year: 2006).*

Barbau-Piednoir, et al. 2010. SYBR® Green qPCR screening methods for the presence of "35S promoter" and "NOS terminator" elements in food and feed products. European Food Research and Technology, 230(3), p. 383. (Year: 2010).*

Pansiot, J., Chaouachi, M., Cavellini, L., Romaniuk, M., Ayadi, M., Bertheau, Y. and Laval, V., 2011. Development of two screening duplex PCR assays for genetically modified organism quantification using multiplex real-time PCR master mixes. European Food Research and Technology, 232(2), pp. 327-334. (Year: 2011).*

Reiting, R., Broll, H., Waiblinger, H.U. and Grohmann, L., 2007. Collaborative study of a T-nos real-time PCR method for screening of genetically modified organisms in food products. Journal für Verbraucherschutz und Lebensmittelsicherheit, 2(2), pp. 116-121. (Year: 2007).*

Samson, M.C., Gullì, M. and Marmiroli, N., 2010. Quantitative detection method for Roundup Ready soybean in food using duplex real-time PCR MGB chemistry. Journal of the Science of Food and Agriculture, 90(9), pp. 1437-1444. (Year: 2010).*

Shepherd, D.N., Mangwende, T., Martin, D.P., Bezuidenhout, M., Kloppers, F.J., Carolissen, C.H., Monjane, A.L., Rybicki, E.P. and Thomson, J.A., 2007. Maize streak virus-resistant transgenic maize: a first for Africa. Plant Biotechnology Journal, 5(6), pp. 759-767. (Year: 2007).*

(Continued)

*Primary Examiner* — Teresa E Strzelecka
*Assistant Examiner* — Olayinka A Oyeyemi

(57) ABSTRACT

The invention relates to a method for quantifying levels of expression and/or quantifying copy number of a heterologous polynucleotide in a transgenic plant using quantitative or real-time polymerase chain reaction (QPCR or real-time PCR), wherein the real-time PCR is performed using a primer set specific to a heterologous terminator sequence operably linked to the heterologous polynucleotide.

19 Claims, 4 Drawing Sheets
Specification includes a Sequence Listing.

(56) References Cited

OTHER PUBLICATIONS

Shou, H., Frame, B.R., Whitham, S.A. and Wang, K., 2004. Assessment of transgenic maize events produced by particle bombardment or Agrobacterium-mediated transformation. Molecular Breeding, 13(2), pp. 201-208. (Year: 2004).*

Uckun, E., 2007. Screening for genetically modified tomatoes & tomato seeds and identification of CRY1AC and SAM-K specific modifications using gene and construct specific PCR (Master's thesis). (Year: 2007).*

Waiblinger et al. 2008. Validation and collaborative study of a P35S and T-nos duplex real-time PCR screening method to detect genetically modified organisms in food products. European Food Research and Technology, 226(5), pp. 1221-1228. (Year: 2008).*

Mano et al. Real-time PCR array as a universal platform for the detection of genetically modified crops and its application in identifying unapproved genetically modified crops in Japan. J Agric Food Chem. Jan. 14, 2009; 57(1 ):26-37. (Year: 2009).*

International Search Report and the Written Opinion of the International Searching Authority for PCT/US2012/047858 dated Oct. 2, 2012.

Abdullah, T et al, "Detection of Genetically Modified Soy in Processed Foods Sold Commercially in Malaysia by PCR-based Method" Food Chemistry, Elsivier Ltd. NL., (2006) vol. 98 (3) 575-579.

Beltran, J. et al, "Quantitive anaylysis of Transgenes in Cassava Plants using Real-Time PCR Technology" In Vitro Cellular & Developmental Biology—Plant (2008) vol. 45 (1) 48-56.

Forte, V. T. et al, "A General Multiplex-PCR Assay for the General Detection of Genetically Modified Soya and Maize" Food Control ( 2005) vol. 16 (6) 535-539.

Ginzinger, D. G., "Gene Quantification using Real-Time quantitative PCR: An Emerging Technology Hits the Mainstream" Experimental Hematology, Elsevier Inc., US, (2002) vol. 30 (1) 503-512.

Hiroshi, Akiyama, et al, "A Screening Method for the Detection of hte 35S Promoter and the Nopaline Synthase Terminator in Genetically Modified Organisms in a Real-Time Multiplex Polymerase Chain Reaction Using High-Resolution Melting-Curve Analysis" Biol. Pharm. Bull (2009) vol. 32 (11) 1824-1829.

Holst-Jensen, A. et al, "PCR Technology for Screening and Quantification of Genetically Modified Organisms (GMOs)" Analytical and Bioanalytical Chemistry (2003) vol. 375 (8) 985-993.

Maccormick, C.A., et al, "Common DNA Sequences with Potential for Detection of Genetically Manipulated Organisms in Food" Journal of Applied Microbiology (1998) vol. 84 (1) 969-980.

Xu, J. et al, "Screening Genetically Modified Organisms Using Multiplex-PCR Coupled with Oligonucleotide Microarray" Biosensors and BioElectronics, Elsevier BV, NL, (2006) vol. 22 (1) 71-77.

De Freitas, Fernando A; et al.: "Structural Characterization and Promoter Activity Analysis of the gamm-kafirin gene from Sorghum," Mol Gen Genet, 1994, vol. 245, pp. 177-186.

International Search Report and Written Opinion for International Application No. PCT/US2012/047901, dated Oct. 12, 2012.

* cited by examiner

SEQUENCE LISTING

<160> NUMBER OF SEQ ID NOS: 13

<210> SEQ ID NO 1
<211> LENGTH: 462
<212> TYPE: DNA
<213> ORGANISM: Sorghum bicolor

<400> SEQUENCE: 1

```
actaactatc tatactgtaa taatgttgta tagccgccgg atagctagct agtttagtca    60
ttcagcggcg atgggtaata ataaagtgtc atccatccat caccatgggt ggcaacgtga   120
gcaatgacct gattgaacaa attgaaatga aagaagaaa tatgttatat gtcaacgaga   180
tttcctcata atgccactga cgacgtgtgt ccaagaaatg tatcagtgat acgtatattc   240 acaattttt tatgacttat actcacaatt tgttttttta ctacttatac tcacaatttg   300
ttgtgggtac cataacaatt tcgatcgaat atatatcaga aagttgacga agtaagctc   360 actcaaaaag ttaaatgggc tgcggaagct gcgtcaggcc caagttttgg ctattctatc   420
cggtatccac gattttgatg gctgagggac atatgttcgc tt                     462
```

<210> SEQ ID NO 2
<211> LENGTH: 18
<212> TYPE: DNA
<213> ORGANISM: Artificial Sequence
<220> FEATURE:
<223> OTHER INFORMATION: SBTerm2F forward primer

<400> SEQUENCE: 2
gccgccggat agctagct                                         18

<210> SEQ ID NO 3
<211> LENGTH: 20
<212> TYPE: DNA
<213> ORGANISM: Artificial Sequence
<220> FEATURE:
<223> OTHER INFORMATION: SBTerm2R reverse primer

<400> SEQUENCE: 3
acccatggtg atggatggat                                       20

<210> SEQ ID NO 4
<211> LENGTH: 20
<212> TYPE: DNA
<213> ORGANISM: Artificial Sequence
<220> FEATURE:
<223> OTHER INFORMATION: SBTerm2 probe

<400> SEQUENCE: 4
tttagtcatt cagcggcgat                                       20

<210> SEQ ID NO 5
<211> LENGTH: 25
<212> TYPE: DNA
<213> ORGANISM: Artificial Sequence
<220> FEATURE:
<223> OTHER INFORMATION: SBTerm1F forward primer

<400> SEQUENCE: 5
ggcgatgggt aataataaag tgtca                                 25

<210> SEQ ID NO 6
<211> LENGTH: 22
<212> TYPE: DNA
<213> ORGANISM: Artificial Sequence
<220> FEATURE:
<223> OTHER INFORMATION: SBTerm1R reverse primer

<400> SEQUENCE: 6
caatcaggtc attgctcacg tt                                    22

<210> SEQ ID NO 7
<211> LENGTH: 22
<212> TYPE: DNA
<213> ORGANISM: Artificial Sequence
<220> FEATURE:
<223> OTHER INFORMATION: SBTerm1 probe

<400> SEQUENCE: 7
aacgtgagca atgacctgat tg                                    22

<210> SEQ ID NO 8
<211> LENGTH: 20
<212> TYPE: DNA
<213> ORGANISM: Artificial Sequence
<220> FEATURE:
<223> OTHER INFORMATION: GUS fwd primer

<400> SEQUENCE: 8
cggaagcaac gcgtaaactc                                       20

<210> SEQ ID NO 9
<211> LENGTH: 21

```
<212> TYPE: DNA
<213> ORGANISM: Artificial Sequence
<220> FEATURE:
<223> OTHER INFORMATION: GUS reverse primer

<400> SEQUENCE: 9
tgtgagcgtc gcagaacatt a                                              21

<210> SEQ ID NO 10
<211> LENGTH: 20
<212> TYPE: DNA
<213> ORGANISM: Artificial Sequence
<220> FEATURE:
<223> OTHER INFORMATION: GUS probe

<400> SEQUENCE: 10
cgcgtccgat cacctgcgtc                                                20

<210> SEQ ID NO 11
<211> LENGTH: 20
<212> TYPE: DNA
<213> ORGANISM: Artificial Sequence
<220> FEATURE:
<223> OTHER INFORMATION: eIF4g-fwd primer

<400> SEQUENCE: 11
cctcctcgag ccatttgaca                                                20

<210> SEQ ID NO 12
<211> LENGTH: 19
<212> TYPE: DNA
<213> ORGANISM: Artificial Sequence
<220> FEATURE:
<223> OTHER INFORMATION: eIF4g reverse primer

<400> SEQUENCE: 12
agggcaggca atctttcgt                                                 19

<210> SEQ ID NO 13
<211> LENGTH: 14
<212> TYPE: DNA
<213> ORGANISM: Artificial Sequence
<220> FEATURE:
<223> OTHER INFORMATION: eIF4g probe

<400> SEQUENCE: 13
acggctccag agct                                                      14
```

METHOD FOR HIGH-THROUGHPUT SCREENING OF TRANSGENIC PLANTS

CROSS REFERENCE TO RELATED APPLICATIONS

This patent application is a continuation of U.S. non-provisional patent application Ser. No. 14/236,461, filed Apr. 4, 2014, which is a national stage entry from international patent application number PCT/US2012/47858, filed Jul. 23, 2012, which claims the benefit of U.S. Provisional Application No. 61/514,052, filed Aug. 2, 2011, the entire contents of each are herein incorporated by reference.

FIELD OF INVENTION

The current invention relates to plant genetic engineering. It relates to methods and compositions for screening transgenic plants for the presence and expression of transgenes.

BACKGROUND

Recent advances in plant genetic engineering have opened new doors to engineer plants to have improved characteristics or traits. These transgenic plants characteristically have recombinant DNA constructs in their genome that have a transgene, operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes.

Regulatory sequences located downstream of coding regions contain signals required for transcription termination and 3' mRNA processing, and are called terminator sequences. The terminator sequences play a key role in mRNA processing, localization, stability and translation (Proudfoot, N, (2004) *Curr Opin Cell Biol* 16:272-278; Gilmartin, G. M. (2005) *Genes Dev.* 19:2517-2521. The 3' regulatory sequences contained in terminator sequences can affect the level of expression of a gene (Ingelbrecht et al. (1989) *Plant Cell* 1:671-680).

One of the challenges of plant genetic engineering is the molecular characterization of the transgenic plants to detect and measure the copy number and the expression of the transgene in the transgenic plant. The transgenic DNA is randomly inserted into the plant genome that can result in gene silencing in transgenic plants with multiple transgene copies integrated into one or more chromosomal locations. Estimation of transgene copy number is thus a vital step of molecular characterization of transgenic plants. Techniques such as southern blotting, comparative genomic hybridization, fluorescence in situ hybridization and PCR using gene-specific primers have been used to measure the copy number of the transgene (Yang et al, *Plant Cell Rep* (2005) 23:759-763). Techniques such as Northern blotting and reverse transcriptase PCR using gene-specific primers are used to quantify expression of the transgene. These techniques can be tedious and prone to errors (Toplak et al. 2004; *Plant Molecular Biology Reporter* 22: 237-250).

Using quantitative or real-time PCR for assaying transgene expression or copy number in transgenic plants has drawbacks, as it can be costly when done with gene specific primers and probes for each different transgene. Moreover, efficiency of each primer set might be different, which would hinder assays for transgene copy number and expression analysis in a high-throughput fashion. If the transgenic plant has an endogenous copy of the gene besides the introduced copy, measuring the expression specifically from the transgene can be difficult.

SUMMARY

The present invention relates to the method for quantifying levels of expression or quantifying copy number of a heterologous polynucleotide in a transgenic plant using quantitative or real-time polymerase chain reaction (QPCR or real-time PCR), wherein the real-time PCR is done using a primer set specific to a heterologous terminator sequence operably linked to the heterologous polynucleotide. The method described in the current invention can be used for assaying levels of expression or copy number of a heterologous polynucleotide in transgenic plants, in a high-throughput manner.

One embodiment of this invention is a method of quantifying the level of expression of a heterologous polynucleotide in a transgenic plant or plant cell, the method comprising the steps of: (a) isolating nucleic acids from a transgenic plant or plant cell, wherein the transgenic plant or plant cell comprises a heterologous polynucleotide operably linked to a heterologous terminator sequence; and (b) quantifying the level of expression of the heterologous polynucleotide by real-time reverse transcriptase polymerase chain reaction using a forward primer and a reverse primer, wherein the forward primer and the reverse primer hybridize to the heterologous terminator sequence or the complement thereof. In another embodiment, the quantification of level of expression of the heterologous polynucleotide is done by quantitative or real-time reverse transcriptase PCR using a probe that hybridizes to the heterologous terminator sequence or the complement thereof.

Another embodiment of the present invention is a method of measuring the copy number of a heterologous polynucleotide in a transgenic plant or plant cell, the method comprising the steps of: (a) isolating nucleic acids from a transgenic plant or plant cell, wherein the transgenic plant or plant cell comprises a heterologous polynucleotide operably linked to a heterologous terminator sequence; and (b) quantifying the copy number of the heterologous polynucleotide by real-time polymerase chain reaction using a forward primer and a reverse primer, wherein the forward primer and the reverse primer hybridize to the heterologous terminator sequence or the complement thereof. In another embodiment, the quantification of copy number of the heterologous polynucleotide is done by quantitative real-time PCR using a probe that hybridizes to the heterologous terminator sequence or the complement thereof.

Another embodiment of this invention is a method of quantifying the level of expression of at least two heterologous polynucleotides present in at least two transgenic plants or plant cells, the method comprising the steps of: (a) isolating nucleic acids from at least two transgenic plants or plant cells, wherein a first transgenic plant or plant cell comprises a first heterologous polynucleotide operably linked to a heterologous terminator sequence, and wherein a second transgenic plant or plant cell comprises a second heterologous polynucleotide operably linked to the heterologous terminator sequence; (b) optionally, isolating nucleic acids from additional transgenic plants or plant cells, wherein each of the additional transgenic plants or plant cells comprises an additional heterologous polynucleotide operably linked to the heterologous terminator sequence; and (c) quantifying the level of expression of the first heterologous polynucleotide, the second heterologous polynucleotide and optional additional heterologous polynucleotides by real-time reverse transcriptase polymerase chain reaction using a forward primer and a reverse primer, wherein the forward primer and the reverse primer hybridize to the heterologous terminator sequence or the complement thereof. In one embodiment, the isolation of nucleic acids from additional transgenic plants or plant cells of step (b) and quantification of level of expression of optional additional heterologous polynucleotides of step (c) is done for at least one hundred additional transgenic plant or plant cells. In one embodiment the copy number of the at least two heterologous polynucleotides present in the at least two transgenic plants or plant cells, wherein each heterologous polynucleotide is operably linked to the heterologous terminator, is quantified using this method.

In another embodiment of any of the methods, the heterologous terminator sequence comprises a SB-GKAF terminator sequence. In another embodiment, the sequence of the heterologous terminator sequence comprises SEQ ID NO:1. In another embodiment, the forward primer, the reverse primer and the probe hybridize to SEQ ID NO:1 or the complement thereof. In another embodiment, the heterologous terminator sequence comprises the SB-GKAF terminator sequence, and the probe hybridizes to the region of the SB-GKAF terminator sequence bounded by the forward primer and the reverse primer. In another embodiment, the heterologous terminator sequence comprises SEQ ID NO:1, the forward primer comprises SEQ ID NO:2, the reverse primer comprises SEQ ID NO:3 and the probe comprises SEQ ID NO:4. In another embodiment, the heterologous terminator sequence comprises SEQ ID NO:1, the forward primer comprises SEQ ID NO:5, the reverse primer comprises SEQ ID NO:6 and the probe comprises SEQ ID NO:7.

In another embodiment of any of the methods, the transgenic plant or plant cell is a maize plant or plant cell.

BRIEF DESCRIPTION OF DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

Figure 3:
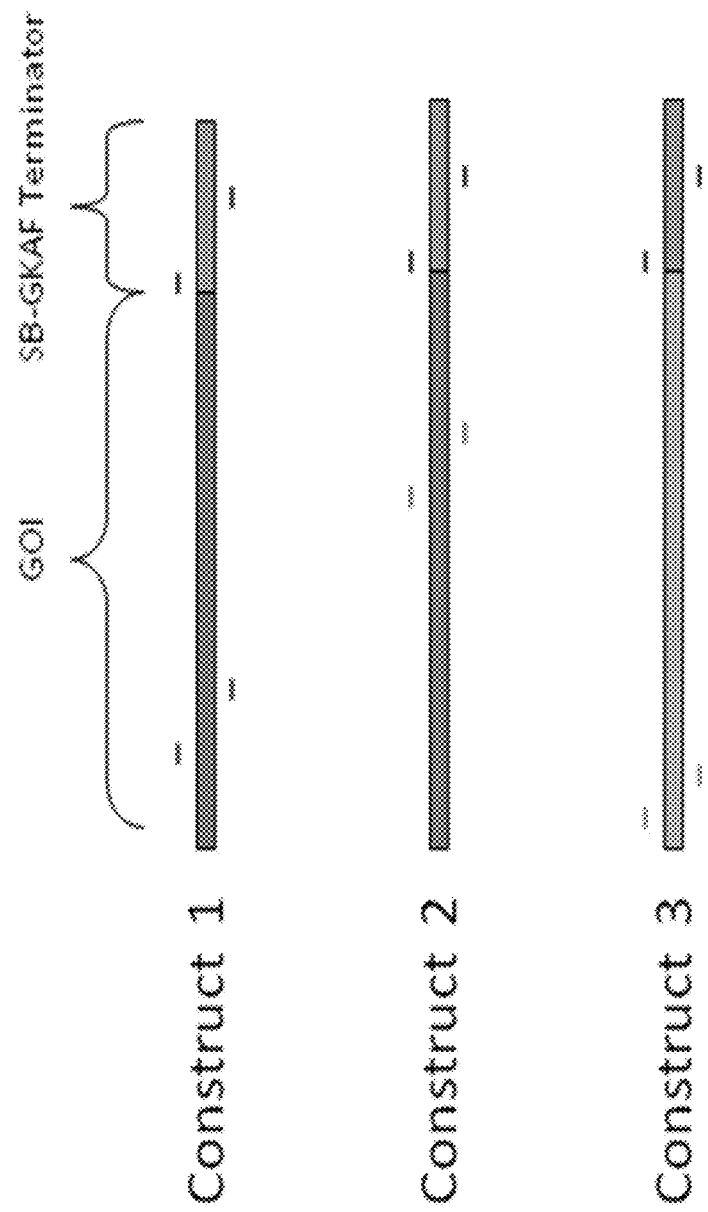

FIG. 3 is a schematic representation showing modes of assaying different transgenes using gene-specific or SB-GKAF terminator-specific primers. Each construct has a unique Gene of Interest ("GOI"), but uses the same terminator. Each construct has a unique inner GOI primer set but uses the same SB-GKAF primer set.

Figure 4:
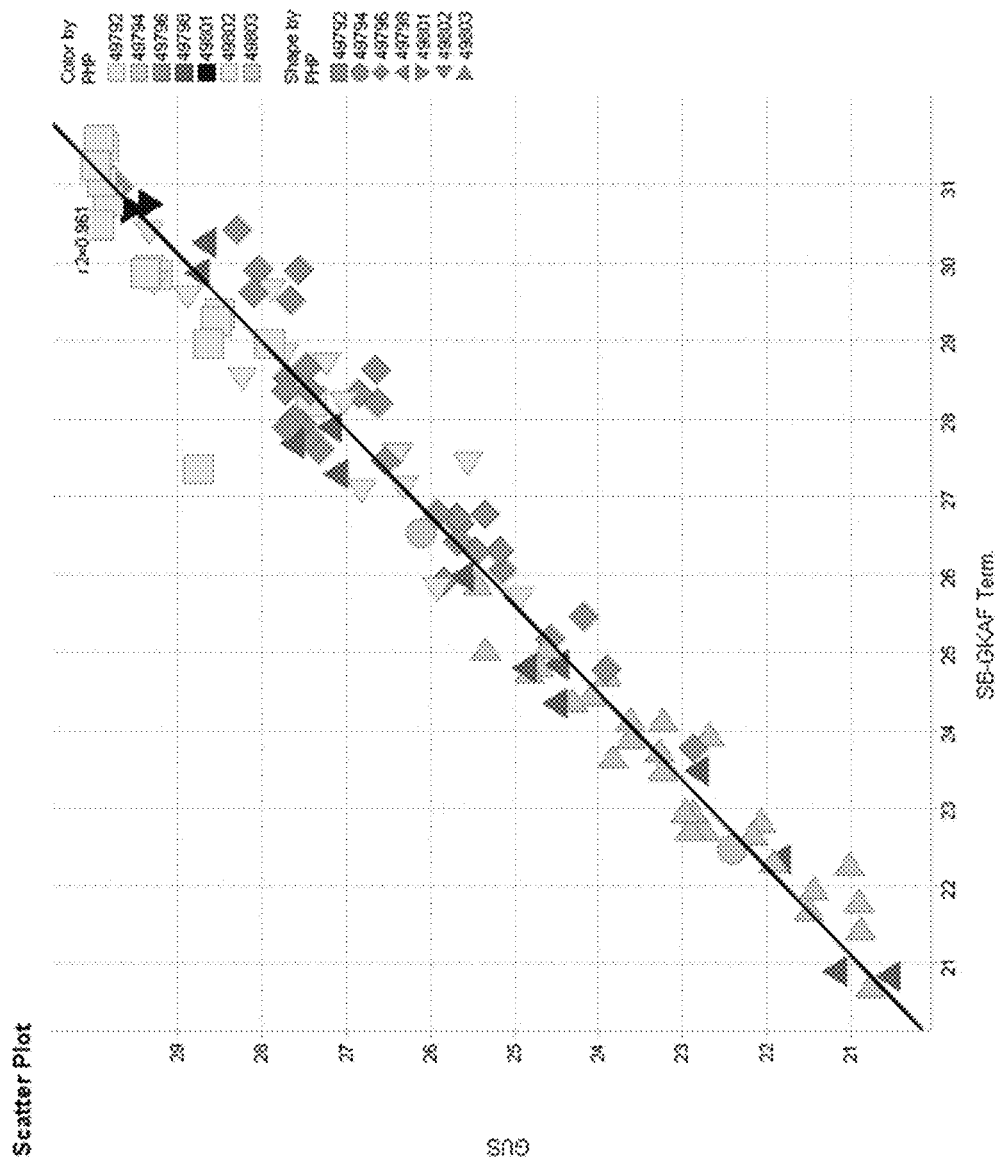

FIG. 4 is a graph showing a QPCR CT comparison using GUS and SB-GKAF terminator primer sets run on the same transgenic samples. GUS CTs are on the Y axis and SB-GKAF CTs are on the X axis.

SEQ ID NO:1 is the sequence of the SB-GKAF terminator.

SEQ ID NO:2 is the sequence of the forward primer, SBTerm2F, used for QPCR. SBTerm2F corresponds to nucleotides 33-50 of SEQ ID NO:1.

SEQ ID NO:3 is the sequence of the reverse primer, SBTerm2R, used for QPCR. SBTerm2R corresponds to the reverse complement of nucleotides 91-110 of SEQ ID NO:1.

SEQ ID NO:4 is the sequence of the SBTerm2 probe used for QPCR. The SBTerm2 probe corresponds to nucleotides 53-72 of SEQ ID NO:1.

SEQ ID NO:5 is the sequence of the forward primer, SBTerm1F, used for QPCR. SBTerm1F corresponds to nucleotides 67-91 of SEQ ID NO:1.

SEQ ID NO:6 is the sequence of the reverse primer, SBTerm1R, used for QPCR. SBTerm1R corresponds to the reverse complement of nucleotides 114-135 of SEQ ID NO:1.

SEQ ID NO:7 is the sequence of the SBTerm1 probe used for QPCR. The SBTerm1 probe corresponds to nucleotides 94-110 of SEQ ID NO:1.

SEQ ID NO:8 is the sequence of the GUS forward primer, GUS-1482-F, used for QPCR.

SEQ ID NO:9 is the sequence of the GUS reverse primer, GUS-1553-R, used for QPCR.

SEQ ID NO:10 is the sequence of the GUS probe, GUS-1509-probe, used for QPCR.

SEQ ID NO:11 is the sequence of the elF4g forward primer, elF4g-F, used for QPCR.

SEQ ID NO:12 is the sequence of the elF4g reverse primer, elF4g-R, used for QPCR.

SEQ ID NO:13 is the sequence of the elF4g probe, elF4g-probe, used for QPCR.

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" includes all products of meiosis and mitosis able to propagate a new plant, including but not limited to, seeds, spores and parts of a plant that serve as a means of vegetative reproduction, such as corms, tubers, offsets, or runners. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

"Progeny" comprises any subsequent generation of a plant.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The terms "entry clone" and "entry vector" are used interchangeably herein.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

Regulatory Sequences:

A recombinant DNA construct (including a suppression DNA construct) of the present invention may comprise at least one regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, but are not limited to, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, but are not limited to, for example, those discussed in U.S. Pat. Nos. 5,608,149; 5,608,144; 5,604,121; 5,569,597; 5,466,785; 5,399,680; 5,268,463; 5,608,142; and 6,177,611.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include, but are not limited to, soybean Kunitz trypsin inhibitor (Kti3, Jofuku and Goldberg, *Plant Cell* 1:1079-1093 (1989)), patatin (potato tubers) (Rocha-Sosa, M., et al. (1989) *EMBO J.* 8:23-29), convicilin, vicilin, and legumin (pea cotyledons) (Rerie, W. G., et al. (1991) *Mol. Gen. Genet.* 259:149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci. U.S.A.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564), and sporamin (sweet potato tuberous root) (Hattori, T., et al. (1990) *Plant Mol. Biol.* 14:595-604). Promoters of seed-specific genes operably linked to heterologous coding regions in chimeric gene constructions maintain their temporal and spatial expression pattern in transgenic plants. Such examples include, but are not limited to, *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, but are not limited to, for example, promoters regulated by light, heat, stress, flooding or drought, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

Recombinant DNA constructs of the present invention may also include other regulatory sequences, including but not limited to, translation leader sequences, introns, and polyadenylation recognition sequences.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

An "enhancing intron" is an intronic sequence present within the transcribed region of a gene which is capable of enhancing expression of the gene when compared to an intronless version of an otherwise identical gene. An enhancing intronic sequence might also be able to act as an enhancer when located outside the transcribed region of a gene, and can act as a regulator of gene expression independent of position or orientation (Chan et. al. (1999) *Proc. Natl. Acad. Sci.* 96: 4627-4632; Flodby et al. (2007) *Biochem. Biophys. Res. Commun.* 356: 26-31).

The intron sequences can be operably linked to a promoter. Promoters may be derived in their entirety from a native gene, or be composed of different elements derived from different promoters found in nature, or even comprise synthetic DNA segments.

"Transcription terminator", "termination sequences", or "terminator" refer to DNA sequences located downstream of a coding sequence in a gene, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence. Transcription termination is the process by which RNA synthesis by RNA polymerase is stopped and both the RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117).

As used herein, a "heterologous terminator" is a terminator sequence that originates from a foreign species, or, if from the same species, is substantially modified from its native form in composition by deliberate human intervention. A "heterologous terminator" is a polynucleotide sequence that exhibits "terminator activity". Examples of such modifications from the native form to get a "heterologous terminator" include, but are not limited to, modifications by adding heterologous sequence elements to a terminator. A "heterologous terminator" as used herein does not correspond to an endogenous terminator that is placed as a non-native chromosomal position.

The terms "SB-GKAF terminator", "GKAF terminator" and "gamma-kafirin terminator" are used interchangeably herein, and each refers to the sequence encoding the 3' untranslated region (3' UTR) of the *Sorghum bicolor* gamma-kafirin gene and the about 300 bp region downstream from the 3' UTR. The sequence of the SB-GKAF terminator is given in SEQ ID NO:1. *Sorghum bicolor* gamma-kafirin gene encodes a gamma-prolamin protein, and the sequence for this gene is given in NCBI GI NO: 671655. Prolamins are the major storage proteins of many cereals. The gamma-kafirin protein, which is the γ-prolamin of *sorghum*, constitutes about 2-5% of total prolamin in *sorghum* endosperm, and is composed of a single polypeptide of 27 kDa (de Freitas F A et al (1994) *Mol Gen Genet* 245:177-186).

The terms "real-time PCR", "quantitative PCR", "quantitative real-time PCR" and "QPCR" are used interchangeably herein, and represent a variation of the standard polymerase chain reaction (PCR) technique used to quantify DNA or RNA in a sample. Using sequence-specific primers and a probe, the relative number or copies of a particular DNA or RNA sequence are determined. The term relative is used since this technique compares relative copy numbers between different genes with respect to a specific reference gene. The quantification arises by measuring the amount of amplified product at each cycle during the PCR process. Quantification of amplified product is obtained using fluorescent hydrolysis probes that measure increasing fluorescence for each subsequent PCR cycle. The "Ct" or "CT" (cycle threshold) is defined as the number of cycles required for the fluorescent signal to cross the threshold (i.e., exceeds background level). DNA/RNA from genes with higher copy numbers will appear after fewer PCR cycles; so the lower a Ct value, the more copies are present in the specific sample. To quantify RNA, QPCR or real-time PCR is preceded by the step of reverse transcribing mRNA into cDNA. This is referred to herein as "real-time RT-PCR" or "quantitative RT-PCR" or "qRT-PCR".

The Taqman method of PCR product quantification uses a fluorescent reporter probe. This is more accurate since the probe is designed to be sequence-specific and will only bind to the specific PCR product. The probe specificity allows for quantification even in the presence of non-specific DNA amplification. This allows for multiplexing, which quantitates several genes in the same tube, by using probes with different emission spectra. Breakdown of the probe by the 5' to 3' exonuclease activity of Taq polymerase removes the quencher and allows the PCR product to be detected.

When plotted on a linear scale, the fluorescent emission increase with PCR cycle number has a sigmoidal shape with an exponential phase and a plateau phase. The plateau phase is determined by the amount of primer in the master mix rather than the nucleotide template. Usually the vertical scale is plotted in a logarithmic fashion, allowing the intersection of the plot with the threshold to be linear and more easily visualized. Theoretically, the amount of DNA doubles every cycle during the exponential phase, but this is affected by the efficiency of the primers used. A positive control using a reference gene, e.g., a "housekeeping" gene that is relatively abundant in all cell types, is also performed to allow for comparisons between samples. The amount of DNA/RNA is determined by comparing the results to a standard curve produced by serial dilutions of a known concentration of DNA/RNA.

As will be evident to one of skill in the art, any heterologous polynucleotide of interest can be operably linked to the heterologous terminator sequence described in the current invention, and the methods of the current invention can be used to assay the expression and copy number of any heterologous polynucleotide of interest. Examples of heterologous polynucleotides of interest that can be operably linked to the heterologous terminator sequence and used for assaying copy number using the methods described in this invention include, but are not limited to, heterologous polynucleotides comprising regulatory elements such as introns, enhancers, promoters, translation leader sequences, protein coding regions, or polynucleotides that can be used to control gene expression. Examples of heterologous polynucleotides of interest that can be operably linked to the heterologous terminator sequence and used for assaying gene expression using the methods described in this invention include, but are not limited to, regulatory elements such as introns, protein coding polynucleotide sequences or polynucleotide sequences that control gene expression. Examples of protein-coding polynucleotide sequences include, but are not limited to disease and insect resistance genes, genes conferring nutritional value, genes conferring yield and heterosis increase, genes that confer male and/or female sterility, antifungal, antibacterial or antiviral genes, and the like. Examples of heterologous polynucleotides that could be used to control gene expression, include, but are not limited to, antisense oligonucleotides, suppression DNA constructs, or nucleic acids encoding transcription factors.

Using gene specific primer sets for quantization of transgene DNA/RNA in transgenic plants has drawbacks, as it can be costly when done in a high throughput manner to have gene-specific primer for each different transgene, efficiency of each primer set might be different, which would hinder transgene copy number and expression assays in a high throughput fashion. Moreover gene-specific primer sets are not directly comparable, QPCR scores of two primer sets might not be equal. Moreover, expression assays using gene-specific primer sets might not be transgene specific; e.g. if the transgene being tested is endogenous to the organism in which it is placed, a gene specific primer set will pick up both transgenic and endogenous expression.

One embodiment of this invention is the use of the method disclosed herein for quantifying expression or copy number of a heterologous polynucleotide in more than one transgenic plant, wherein each transgenic plant comprises a recombinant construct comprising a different heterologous polynucleotide operably linked to a heterologous terminator comprising the same polynucleotide sequence. In one embodiment the method disclosed herein is used for quantifying expression and copy number of a heterologous polynucleotide in many transgenic plants, in a high-throughput manner, wherein each transgenic plant comprises a recombinant construct comprising a different heterologous polynucleotide operably linked to a heterologous terminator comprising the same polynucleotide sequence. In one embodiment the heterologous terminator is the SB-KAF terminator. In one embodiment, the transgenic plants are maize plants.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook"). Embodiments of the current invention include:

One embodiment of this invention is a method of quantifying the level of expression of a heterologous polynucleotide in a transgenic plant or plant cell, the method comprising the steps of: (a) isolating nucleic acids from a transgenic plant or plant cell, wherein the transgenic plant or plant cell comprises a heterologous polynucleotide operably linked to a heterologous terminator sequence; and (b) quantifying the level of expression of the heterologous polynucleotide by real-time reverse transcriptase polymerase chain reaction using a forward primer and a reverse primer, wherein the forward primer and the reverse primer hybridize to the heterologous terminator sequence or the complement thereof. In another embodiment, the quantification of level of expression of the heterologous polynucleotide is done by quantitative reverse transcriptase real-time PCR using a probe that hybridizes to the heterologous terminator sequence or the complement thereof.

Another embodiment of the present invention is a method of measuring the copy number of a heterologous polynucleotide in a transgenic plant or plant cell, the method comprising the steps of: (a) isolating nucleic acids from a transgenic plant or plant cell, wherein the transgenic plant or plant cell comprises a heterologous polynucleotide operably linked to a heterologous terminator sequence; and (b) quantifying the copy number of the heterologous polynucleotide by real-time polymerase chain reaction using a forward primer and a reverse primer, wherein the forward primer and the reverse primer hybridize to the heterologous terminator sequence or the complement thereof. In anther embodiment, the quantification of copy number of the heterologous polynucleotide is done by quantitative real-time PCR using a probe that hybridizes to the heterologous terminator sequence or the complement thereof.

Another embodiment of the invention is a method of quantifying the level of expression of at least two heterologous polynucleotides present in at least two transgenic plants or plant cells, the method comprising the steps of: (a) isolating nucleic acids from at least two transgenic plants or plant cells, wherein a first transgenic plant or plant cell comprises a first heterologous polynucleotide operably linked to a heterologous terminator sequence, and wherein a second transgenic plant or plant cell comprises a second heterologous polynucleotide operably linked to the heterologous terminator sequence; (b) optionally, isolating nucleic acids from additional transgenic plants or plant cells, wherein each of the additional transgenic plants or plant cells comprises an additional heterologous polynucleotide operably linked to the heterologous terminator sequence; and (c) quantifying the level of expression of the first heterologous polynucleotide, the second heterologous polynucleotide and optional additional heterologous polynucleotides by real-time reverse transcriptase polymerase chain reaction using a forward primer and a reverse primer, wherein the forward primer and the reverse primer hybridize to the heterologous terminator sequence or the complement thereof. In one embodiment, the isolation of nucleic acids from additional transgenic plants or plant cells of step (b) and quantification of level of expression of optional additional heterologous polynucleotides of step (c) is done for at least 100, at least 200, at least 300, at least 400, at least 500, at least 600, at least 700, at least 800, at least 900, or at least 1000 additional transgenic plants or plant cells. In one embodiment the copy number of the at least two heterologous polynucleotides present in the at least two transgenic plants or plant cells, wherein each heterologous polynucleotide is operably linked to the heterologous terminator, is quantified using this method.

In another embodiment of any of the methods described herein, the heterologous terminator sequence comprises a SB-GKAF terminator sequence. In another embodiment, the sequence of the heterologous terminator sequence comprises SEQ ID NO:1. In another embodiment, the forward primer, the reverse primer and the probe hybridize to SEQ ID NO:1 or the complement thereof. In another embodiment, the heterologous terminator sequence comprises the SB-GKAF terminator sequence, and the probe hybridizes to the region of the SB-GKAF terminator sequence bounded by the forward primer and the reverse primer. In another embodiment, the heterologous terminator sequence comprises SEQ ID NO: 1, the forward primer comprises SEQ ID NO:2, the reverse primer comprises SEQ ID NO:3 and the probe comprises SEQ ID NO:4. In another embodiment, the heterologous terminator sequence comprises SEQ ID NO:1, the forward primer comprises SEQ ID NO:5, the reverse primer comprises SEQ ID NO:6 and the probe comprises SEQ ID NO:7. In another embodiment, the heterologous terminator sequence comprises SEQ ID NO:1, the forward primer comprises SEQ ID NO:2, the reverse primer comprises SEQ ID NO:6 and the probe comprises at least one sequence selected from the group consisting of SEQ ID NO:4 and SEQ ID NO:7. In another embodiment, any of the methods described herein, wherein the plant or plant cell is a monocotyledonous or dicotyledonous plant or plant cell, for example, a maize or soybean plant or plant cell. The plant or plant cell may also be from sunflower, *sorghum*, canola, wheat, alfalfa, cotton, rice, barley, millet, sugar cane or switchgrass. The invention encompasses regenerated, mature and fertile transgenic plants generated using the methods described above, transgenic seeds produced therefrom, T1 and subsequent generations.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Assaying Transgene Expression in Maize Using Sequence from a SB-GKAF Terminator

The sequence of the SB-GKAF terminator (gamma-kafirin terminator from Sorghum bicolor) is given in SEQ ID NO:1. Like the majority of all gene terminators, the SB-GKAF terminator is known to be affected by post-transcriptional mRNA processing. In order to produce a reliable SB-GKAF terminator-specific QPCR (Quantitative Polymerase Chain Reaction or "real time PCR") primer set, it was required to determine where the terminator would be processed and a poly-A tail would be added by post-transcriptional processing. Without the knowledge of this location, there would have been the risk of creating a QPCR based assay that is pre-transcriptional processing mRNA specific, missing all post-transcriptional mRNA. By finding and comparing the sequence of SB-GKAF terminator given in SEQ ID NO:1 to sequences of other very similar SB-GKAF EST clones in Pioneer's internal data set, the prediction about where the SB-GKAF terminator would be clipped could be made. This dipping site was then further confirmed by identifying the polyA recognition sequence. The "safe zone" sequence, upstream of the predicted terminator dipping site, was used to design the TaqMan primer/probe set. This primer/probe set was named SBTerm2.

Shown below is the sequence of the SB-GKAF terminator (SEQ ID NO:1). The binding sites for the SBTerm2 forward and reverse primers (SEQ ID NO:2 and SEQ ID NO:3, respectively) are depicted in bold capital letters in the sequence below. The SBTerm2 probe (SEQ ID NO:4) binding site is shown in italics and bold letters. The poly (A) recognition sequence is shown in lower case and bold. The sequence predicted to be clipped off during mRNA processing is shown in italics.

```
SB-GKAF terminator (SEQ ID NO: 1):
actaactatctatactgtaataatgttgtataGCCGCCGGATAGC TAGCTagtttagtcattcagcggcgatgggtaataataaagtgt cATCCATCCATCACCATGGGTggcaacgtgagcaatgacctgatt
```

-continued
```
gaacaaattgaaatgaaaagaagaaatatgttatatgtcaacgag atttcctcataatgccactgacgacgtgtgtccaagaaatgtatc agtgatacgtatattcacaattttttttatgacttatactcacaat ttgttttttactacttatactcacaatttgttgtgggtaccata acaatttcgatcgaatatatatcagaaagttgacgaaagtaagct cactcaaaaagttaaatgggctgcggaagctgcgtcaggcccaag ttttggctattctatccggtatccacgatttttgatggctgaggga catatgttcgctt
```

Primer Design and Validation:

The SBTerm2 primer/probe set is Taqman based. For testing, the probe was labeled with a VIC dye, but other dyes also can be used. Sequences of the SBTerm2 primer/probe are shown below (Table 1).

TABLE 1

SBTerm2 Primer and Probe Names, Sequences, and Dye Information

| Primer/Probe | Sequence | Dye |
|---|---|---|
| SBTerm2F (SEQ ID NO: 2) | GCCGCCGGATAGCTAGCT | — |
| SBTerm2R (SEQ ID NO: 3) | ACCCATGGTGATGGATGGAT | — |
| SBTerm2 Probe (SEQ ID NO: 4) | TTTAGTCATTCAGCGGCGAT | VIC |

The first step in validating the SBTerm2 primer/probe QPCR assay was by testing the efficiency of the primer/probe set. To do this, a plasmid containing the SB-GKAF terminator was serial diluted, and the dilutions were used as PCR templates for the SBTerm2 primer/probe set.

TABLE 2

The Slope and Efficiency Results of Primer/Probe Set SBTerm2

| Primer set | Template | Slope | Efficiency |
|---|---|---|---|
| SBTerm2 | PHP31801 | −3.580 | 0.903 |

Figure 1:
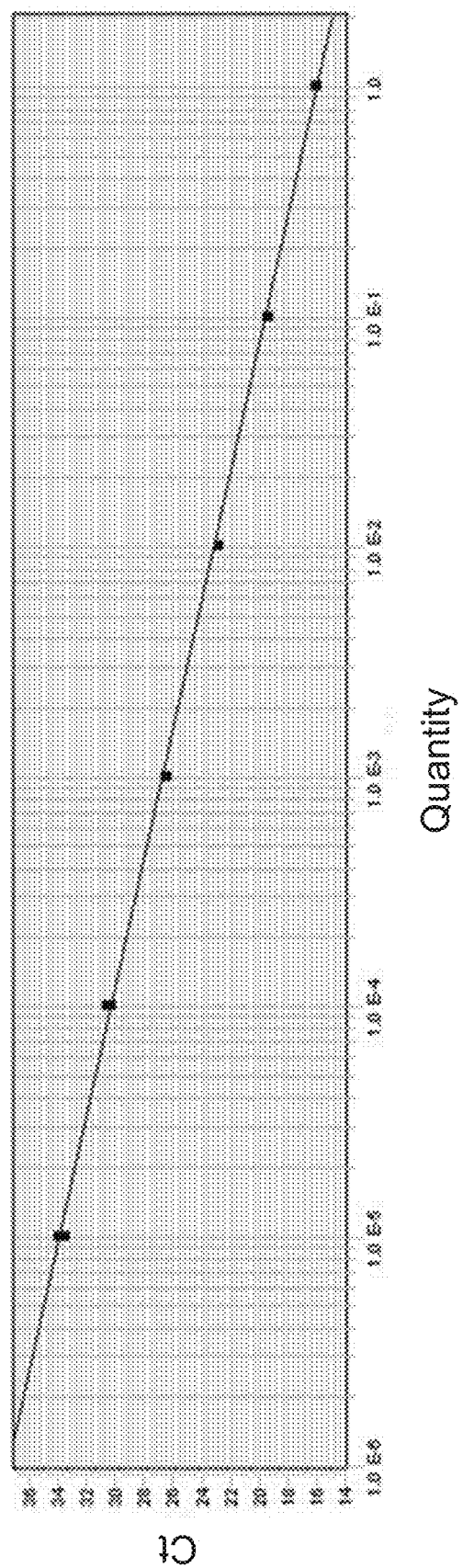
FIG. 1 is a graph showing the efficiency curve of the SBTerm2 primer/probe set.
Figure 2:
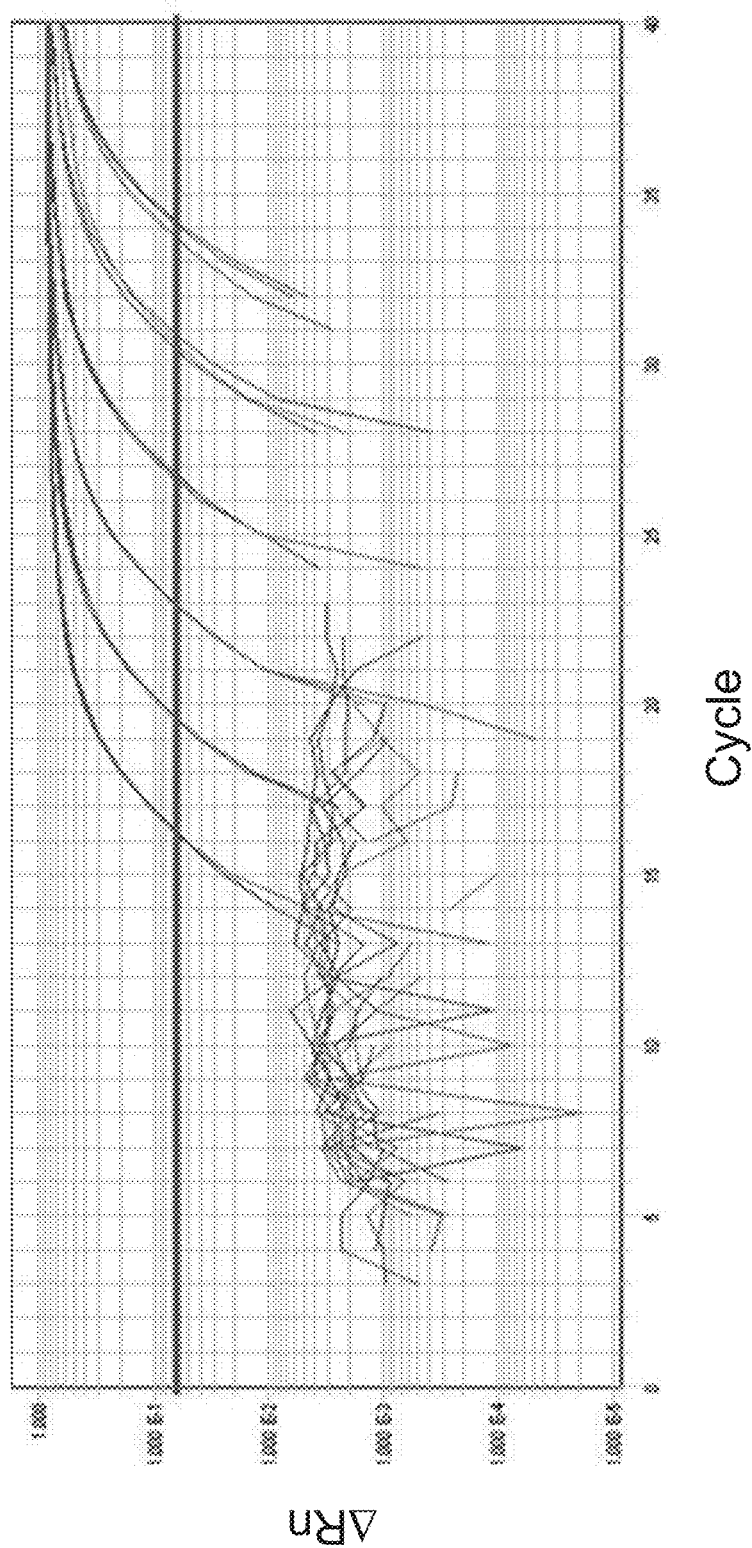
FIG. 2 is a graph showing the amplification plot of the SBTerm2 primer/probe set.

The efficiency test proved to be successful (FIG. 1). The amplifications for primer/probe set SBTerm2 were clearly discernable (FIG. 2), and the efficiency was found to be about 90% (Table 2).

Gene of Interest (GOI)-Specific Vs. SB-GKAF Terminator-Specific Primer Sets:

Although a terminator is considered part of a gene, "gene-specific" or "GOI-specific" primer sets, used interchangeably herein, refer to primer sets that are in the portion of the gene upstream of the terminator. It is standard practice to assay gene expression by designing unique gene-specific primer sets. For high throughput assays of transgene expression in transgenic maize plants, this can amount to literally thousands of genes, each with its own unique primer set. This method of assaying gene expression is costly and has many drawbacks. The drawbacks of using gene-specific primer sets include cost, since each unique GOI required its own primer set. Additionally, there were efficiency variations since GOI-specific primer sets were not directly comparable; the QPCR score of one primer set might not equal the QPCR score of another primer set. Moreover, a gene-specific primer set is not necessarily transgene specific; e.g., if the transgene being tested is endogenous to the organism in which it is placed, a gene-specific primer set will pick up both transgenic and endogenous expression.

If each of the Genes of Interest (GOIs) in a number of transgenic maize lines had a universal sequence transcribed, and if that sequence was unique with respect to each transformed plant's genome, then just one primer set could be designed. This approach would solve the drawbacks of having to use gene-specific primer sets. Furthermore, a vast majority of transgenic GOIs are ESTs. ESTs come from mRNA transcripts which naturally do not contain full terminator sequences. Because ESTs are missing a full terminator, when ESTs are used as a transgenic gene a terminator must be supplied for reliable transcription termination.

Materials and Methods:
Sample Collection and Preparation:

All of the QPCRs mentioned below were done using transgenic Gaspe Flint derived maize lines containing GOIs. The transgenic Gaspe Flint derived maize lines containing GOIs may or may not have been challenged with abiotic stresses. All of the samples were taken from corn and were collected by leaf punching followed by immediate sample freezing using dry ice. All transgenic samples contain an over-expressed GOI that uses the SB-GKAF terminator for transcription termination. All transgenes in this study were native to corn. Because the GOIs were all native to corn, after transformation, each transgenic plant would have at least two copies of the GOI (the endogenous and the transgenic), and each non-transgenic plant only has one copy of the GOI (the endogenous).

From each sample, the mRNA was extracted, the genomic DNA was degraded, and cDNA was synthesized. From the cDNA, two QPCRs were done: a SB-GKAF terminator specific assay (SBTerm2), and an inner GOI specific assay (FIG. 3).

Correlation Analysis:

After the GOI and SB-GKAF terminator specific primer set QPCRs were done, a construct specific correlation comparison was conducted. The correlation comparison was done to illustrate that a SB-GKAF terminator specific primer set can be used to detect transgenic expression, by comparison to the standard GOI specific QPCR method. The reasoning of the correlation analysis was that because the two PCRs are specific for the same transcription fragment (FIG. 3), any changes in expression of the GOI specific QPCR should also have corresponding changes in the SB-GKAF terminator specific QPCR.

Endogenous GOI Expression Interference:

In this study, the correlation comparison of the two primer sets can be thrown off if a sample is included in the analysis that does not have their transgenic GOI expressing at a level higher than the endogenous gene. As stated above, all of the transgenic GOIs in this study are native to the transformed organism. This can throw off the correlation analysis because even though the SBTerm2 primer set is specific for the SB-GKAF terminator, the inner GOI primer set not only detects transgenic expression (as shown in FIG. 3), but also detects endogenous GOI expression (not shown). This would not be a problem if the transgenic GOIs were completely foreign in sequence, since then, like with the SB-GKAF terminator primer set, the inner GOI specific primer set would be specific to the transgene.

To bypass this error, the upper limit of endogenous expression was detected and only the samples expressing their transgene beyond this point were focused on. The idea was that even if the endogenous gene expression were changing (which could throw off correlations), it would have made little or no difference if the transgenic GOI was expressing at a much higher level and only those much higher levels were used in the correlation analysis. The endogenous GOI expression zone was found by identifying the lowest inner GOI primer set CT scores of non-transgenics or transgenic non-expressors, if available. This lowest CT value was then used to set a threshold CT score, and any transgenic samples that had a higher inner GOI CT scores (lower expression) than this threshold were not used in the correlation analysis, because it was deemed to not be expressing the transgene beyond the "endogenous zone".

In addition to transgenic samples, QPCRs were also done on non-transgenic samples, or endogenous expression levels were deduced by searching for transgenic samples not expressing the transgene, as found by not expressing the SB-GKAF terminator specific primer set. If neither of these two options for finding endogenous GOI expression level were available, all of that construct's transgenic samples were used in the inner GOI primer set vs. SB-GKAF primer set correlation comparison.

Results:

Thirty-three transgenic maize lines with unique constructs were tested for transgene expression using GOI specific primers and SB-GKAF terminator specific primers. Multiple events were tested for each construct. Table 3 depicts the calculation of the SBTerm2-GOI CT Correlation Coefficient data for one construct. Table 4 depicts the SBTerm2-GOI CT Correlation Coefficient for the 33 constructs tested and average of the SBTerm2-GOI CT Correlation Coefficient.

Table Heading Explanations:

1. Sample—Each sample represents a unique transformation event or a unique non-transgenic control plant.
2. Construct—Each construct refers to a unique vector. Each vector is identical, except for the GOI that is being over-expressed. Constructs labeled "NT" are non-transgenic, and were not transformed with a vector.
3. Inner GOI Primer set—Each construct had a unique GOI, and each GOI has a unique inner gene primer set. Each transgenic GOI comes from an EST. After vector insertion, each EST uses the SB-GKAF terminator. Non-transgenic controls do not have transgenic GOIs, but like the transgenic samples, do have the endogenous GOI.
4. SBTerm2 CT—The QPCR CT score for the SB-GKAF terminator specific primer set SBTerm2.
5. Inner GOI Primer Set CT—The QPCR CT score of whatever inner GOI primer set was run for a particular sample.
6. Used in Correlation—States whether or not a sample's SBTerm2 and inner GOI CT scores were used in the correlation analysis. Along with non-transgenic samples, samples showing GOI expression at endogenous levels were not included in the correlation analysis.
7. GOI CT Cutoff—The cutoff inner GOI primer set CT score used as a threshold. This threshold is the highest level of endogenous expression (lowest CT score) found in non-transgenic samples or transgenic samples not expressing transgenic GOI (as found by not expressing SBTerm2). Any sample that does not have an inner GOI primer set CT score below the threshold CT is considered to not be expressing their transgenic GOI higher than natural levels, and thus are not to be included in the correlation analysis.

8. SBTerm2-GOI CT Correlation Coefficient—The correlation coefficient found using the specified transgenic samples included in analysis.

TABLE 3

CT and SBTerm2-GOI CT Correlation Coefficient Data for a Specific Transgenic Construct

| Sample | Construct | Inner GOI Primer Set | SBTerm2 CT | Inner GOI Primer Set CT | Used in Correlation? |
|---|---|---|---|---|---|
| Transgenic event 1 | 1 | TR004 | 25.487 | 20.586 | Yes |
| Transgenic event 2 | 1 | TR004 | 25.151 | 20.701 | Yes |
| Transgenic event 3 | 1 | TR004 | 25.066 | 20.875 | Yes |
| Transgenic event 4 | 1 | TR004 | 25.474 | 20.919 | Yes |
| Transgenic event 5 | 1 | TR004 | 25.984 | 21.461 | Yes |
| Transgenic event 6 | 1 | TR004 | 24.954 | 21.572 | Yes |
| Transgenic event 7 | 1 | TR004 | 26.129 | 21.834 | Yes |
| Transgenic event 8 | 1 | TR004 | 26.898 | 21.957 | Yes |
| Transgenic event 9 | 1 | TR004 | 26.460 | 22.196 | Yes |
| Transgenic event 10 | 1 | TR004 | 26.532 | 22.237 | Yes |
| Transgenic event 11 | 1 | TR004 | 26.372 | 22.341 | Yes |
| Transgenic event 12 | 1 | TR004 | 26.902 | 22.354 | Yes |
| Transgenic event 13 | 1 | TR004 | 28.315 | 23.054 | Yes |
| Transgenic event 14 | 1 | TR004 | 27.286 | 23.090 | Yes |
| Transgenic event 15 | 1 | TR004 | 29.663 | 24.790 | Yes |
| | | | GOI CT cut off | 30.00 | |
| | | | SBTerm2-GOI CT Correlation Coefficient | 0.939 | |

TABLE 4

Summary and Average of SBTerm2-GOI CT Correlation Coefficient Data for 33 Transgenic Constructs

| Construct | Primer set | SBTerm2-GOI CT Correlation Coefficient |
|---|---|---|
| 1 | TR004 | 0.939 |
| 2 | TR005 | 0.981 |
| 3 | TR038 | 0.936 |
| 4 | TR032 | 0.983 |
| 5 | TR034 | 0.813 |
| 6 | TR026 | 0.994 |
| 7 | TR023 | 0.902 |
| 8 | TR064 | 0.910 |
| 9 | TR053 | 0.874 |
| 10 | TR055 | 0.878 |
| 11 | TR008 | 0.880 |
| 12 | TR010 | 0.969 |
| 13 | TR072 | 0.981 |
| 14 | TR018 | 0.914 |
| 15 | TR002 | 0.899 |
| 16 | TR069 | 0.968 |
| 17 | TR079 | 0.873 |
| 18 | TR095 | 0.865 |
| 19 | TR084 | 0.757 |
| 20 | TR101 | 0.734 |
| 21 | TR093 | 0.838 |
| 22 | TR100 | 0.720 |
| 23 | TR086 | 0.973 |
| 24 | TR108 | 0.917 |
| 25 | TR104 | 0.932 |
| 26 | TR083 | 0.919 |
| 27 | TR082 | 0.842 |
| 28 | TR109 | 0.816 |
| 29 | TR110 | 0.917 |
| 30 | TR122 | 0.891 |
| 31 | TR123 | 0.997 |
| 32 | TR126 | 0.410 |
| 33 | TR127 | 0.819 |
| | Ave | 0.88 |

A distinct advantage of the SB-Term terminator primer set QPCR assay is that it is transgene specific. The ability to decipher transgenic expressers from transgenic non-expressors provides a tremendous advantage when compared to the use of only inner GOI primer sets.

The level of endogenous GOI expression levels could be inferred from 21 of the constructs that had non-transgenic controls included, and 3 constructs that contained transgenic samples that were not expressing the transgene (as was evident by having SBTerm2 CT scores in the 30s). For these 24 constructs, a threshold value could be adequately made to exclude any transgenic samples that were not expressing the transgene at higher than endogenous levels. The remaining 10 constructs, in which endogenous expression levels could not be inferred, had all samples included in their construct specific correlation analysis.

As is evident from the correlation coefficients, it appears that the expression variations of the inner GOI specific primer sets and the SBTerm2 primer set change in a correlated manner. These high value positive correlations showed that both primer sets are monitoring the expression of the same transcripts. There were 17 constructs that had a correlation above 90%, 13 constructs between 80-90%, 3 constructs between 70-80%, and one construct below 70%. These are high correlation values, considering the error of endogenous expression interference and primer set efficiency variation. The correlation coefficients with the most weight might be constructs that had little or no endogenous GOI expression, since they would be likely to have the least amount of endogenous GOI expression interference. The correlation coefficient values of these select constructs were all 80% or above.

While all of the constructs in these experiments were over-expressing the GOI, the SB-GKAF terminator can also be used in RNAi knockdown constructs. However, one would not expect correlated values between inner GOI primer sets and SB-GKAF terminator specific primer sets, because the knock down machinery would be playing too large of an interfering role on mRNA transcripts.

Example 2

Alternative Primer/Probe Set for Assaying Transgene Expression in Maize

Another primer/probe set, designated SBTerm1, was used to assay transgene expression in maize. The SBTerm1 and SBTerm2 primer/probe sets were found to have similar amplification efficiencies. Sequences of the SBTerm1 primer/probe set are shown below (Table 5).

TABLE 5

SBTerm1 Primer and Probe Names and Corresponding Sequences

| Primer/Probe | Sequence |
|---|---|
| SBTerm1F (SEQ ID NO: 5) | GGCGATGGGTAATAATAAAGTGTCA |
| SBTerm1R (SEQ ID NO: 6) | CAATCAGGTCATTGCTCACGTT |
| SBTerm1 Probe (SEQ ID NO: 7) | CATCCATCACCATGGGT |

Example 3

Assaying Copy Number in Maize Using Sequence from a SB-GKAF Terminator

Primers and probe sequence specific to the SB-GKAF terminator sequence can also used to determine copy number of a transgene with QPCR in a high-throughput assay.

For zygosity or copy number assays, a known fully segregated homozygous housekeeping gene that has two copies can be compared to unknown samples that are either homozygous, heterozygous or have no copies of the transgene tested. The relative comparison of the samples would determine the copy number present for the unknown sample.

Reactions can be carried out for 40 PCR cycles on an ABI Taqman 7900 PCR instrument, with cycling parameters of 95° C. for 2 min, 95° C. for 10 sec, 60° C. for 1 min. Fluorescent measurements can be taken from each well at each of the 40 cycles for both the terminator sequence derived from the *Sorghum bicolor* GKAF (SB-GKAF) gene and the endogenous adh1 control. Samples can be scored for relative copy number by subtracting the cycle threshold values from the cycle threshold value of the endogenous control. The cycle threshold (Ct) can be determined, and the delta Ct can be calculated relative to the known endogenous control value.

Example 4

Assaying GUS Transgene Expression in Maize Using Sequence from a SB-GKAF Terminator An SB-GKAF terminator expression assay was also done on transgenic maize plants transformed with constructs containing a GUS protein-coding sequence operably linked to an SB-GKAF terminator. GUS is not endogenous to corn. The number of samples assayed was 108, which included two tissues (root and leaf) and seven Promoter::GUS::SB-GKAF constructs. A number of different promoters were used to drive GUS expression. Copy number analysis indicated that for each transgenic line the T-DNA was a single, non-complex insert. For each sample, we ran QPCR primer sets on the following three elements: a reference gene (eIF4g), GUS, and the SB-GKAF terminator. The sequences of the eIF4g and GUS primers sets and probes are given in Table 6. The sequences primers and probe used for SB-GKAF are given in Table 1 (SBTerm2F, SBTerm2R and SBTerm2 probe; SEQ ID NO:2, 3 and 4 respectively). The results are given in Table 7 and in FIG. 4. FIG. 4 shows a QPCR CT comparison using GUS and SB-GKAF terminator primer sets run on the same transgenic samples. GUS CTs are on the Y axis and SB-GKAF CTs are on the X axis. The correlation coefficient for this is 0.9805 with an R^2 of 0.961. As is evident from the correlation coefficient, expression levels based on the GUS-specific primer set and the SBTerm2 primer set are correlated. This high positive correlation value shows that either primer sets can be used to determine expression levels of the GUS transgene.

TABLE 6 eIF4g and GUS Primer and Probe Names, Sequences, and Dye Information

| Primer/Probe | Sequence | Dye |
|---|---|---|
| GUS-1482-F (SEQ ID NO: 8) | CGGAAGCAACGCGTAAACTC | — |
| GUS-1553-R (SEQ ID NO: 9) | TGTGAGCGTCGCAGAACATTA | — |
| GUS-1509-P (SEQ ID NO: 10) | CGCGTCCGATCACCTGCGTC | FAM |
| eIF4-g-F (SEQ ID NO: 11) | CCTCCTCGAGCCATTTGACA | — |
| eIF4-g-R (SEQ ID NO: 12) | AGGGCAGGCAATCTTTCGT | — |
| eIF4-g-P (SEQ ID NO: 13) | ACGGCTCCAGAGCT | VIC |

TABLE 7

| Tissue type | Sample name | PHP | Ct-Reference (eIF4g) | CT-GUS | CT-SBGKAF |
|---|---|---|---|---|---|
| Leaf | AP0140D01L.16 | 49798 | 21.92 | 20.57 | 20.84 |
| Leaf | AP0140F01L.16 | 49803 | 20.87 | 20.78 | 20.71 |
| Root | AP0140F01R.8 | 49803 | 19.57 | 20.89 | 21.45 |
| Leaf | AP0140F01L.9 | 49803 | 21.61 | 20.92 | 21.81 |
| Root | AP0140F01R.16 | 49803 | 19.59 | 21.02 | 22.28 |
| Leaf | AP0140D01L.1 | 49798 | 22.05 | 21.19 | 20.9 |
| Root | AP0140F01R.10 | 49803 | 19.64 | 21.45 | 21.97 |
| Leaf | AP0140F01L.12 | 49803 | 23.63 | 21.5 | 21.7 |
| Leaf | AP0140D01L.8 | 49798 | 21.65 | 21.86 | 22.34 |
| Root | AP0140F01R.7 | 49803 | 19.75 | 21.92 | 22.32 |
| Root | AP0140F01R.6 | 49803 | 20.26 | 22.07 | 22.83 |
| Leaf | AP0140F01L.7 | 49803 | 20.66 | 22.17 | 22.68 |
| Leaf | AP0140B01L.9 | 49794 | 22.72 | 22.42 | 22.46 |
| Root | AP0140F01R.9 | 49803 | 20.64 | 22.69 | 23.96 |
| Leaf | AP0140F01L.8 | 49803 | 21.91 | 22.74 | 22.73 |
| Leaf | AP0140D01L.15 | 49798 | 22.42 | 22.85 | 23.48 |
| Root | AP0140C01R.8 | 49796 | 20.02 | 22.87 | 23.77 |
| Leaf | AP0140F01L.1 | 49803 | 21.73 | 22.88 | 22.96 |
| Leaf | AP0140F01L.2 | 49803 | 21.7 | 22.92 | 22.74 |
| Root | AP0140F01R.14 | 49803 | 20.46 | 22.96 | 22.97 |
| Leaf | AP0140F01L.5 | 49803 | 23.51 | 23.23 | 23.5 |
| Root | AP0140F01R.1 | 49803 | 20.23 | 23.24 | 24.13 |
| Root | AP0140F01R.15 | 49803 | 20.12 | 23.27 | 23.75 |
| Root | AP0140F01R.4 | 49803 | 21.06 | 23.61 | 24.14 |
| Root | AP0140F01R.13 | 49803 | 20.83 | 23.61 | 23.92 |
| Leaf | AP0140F01L.14 | 49803 | 23.54 | 23.83 | 23.67 |
| Root | AP0140F01R.11 | 49803 | 21.3 | 23.9 | 24.71 |
| Root | AP0140C01R.9 | 49796 | 20.19 | 23.91 | 24.78 |
| Leaf | AP0140F01L.6 | 49803 | 22.84 | 24.08 | 24.47 |
| Leaf | AP0140C01L.9 | 49796 | 22.99 | 24.18 | 25.45 |
| Leaf | AP0140F01L.15 | 49803 | 22.83 | 24.31 | 24.39 |
| Leaf | AP0140D01L.10 | 49798 | 22.84 | 24.5 | 24.84 |
| Leaf | AP0140D01L.14 | 49798 | 24.11 | 24.51 | 24.34 |
| Leaf | AP0140C01L.8 | 49796 | 21.87 | 24.57 | 25.16 |
| Leaf | AP0140F01L.4 | 49803 | 23.68 | 24.62 | 25.06 |
| Root | AP0140F01R.5 | 49803 | 20.82 | 24.71 | 24.84 |

TABLE 7-continued

| Tissue type | Sample name | PHP | Ct-Reference (eIF4g) | CT-GUS | CT-SBGKAF |
|---|---|---|---|---|---|
| Leaf | AP0140F01L.3 | 49803 | 23.74 | 24.81 | 24.75 |
| Leaf | AP0140D01L.6 | 49798 | 23.99 | 24.88 | 24.8 |
| Root | AP0140G01R.10 | 49802 | 21.28 | 24.93 | 25.69 |
| Root | AP0140C01R.7 | 49796 | 21.91 | 25.15 | 26.06 |
| Root | AP0140C01R.16 | 49796 | 20.67 | 25.18 | 26.31 |
| Leaf | AP0140C01L.1 | 49796 | 22.01 | 25.36 | 26.77 |
| Root | AP0140F01R.12 | 49803 | 22.3 | 25.36 | 25.04 |
| Leaf | AP0140F01L.13 | 49803 | 23.81 | 25.45 | 25.89 |
| Leaf | AP0140C01L.15 | 49796 | 22.76 | 25.46 | 26.3 |
| Root | AP0140G01R.7 | 49802 | 20.12 | 25.56 | 27.42 |
| Leaf | AP0140D01L.7 | 49798 | 23.48 | 25.63 | 25.98 |
| Root | AP0140C01R.15 | 49796 | 20.65 | 25.66 | 26.65 |
| Leaf | AP0140C01L.16 | 49796 | 22.04 | 25.67 | 26.43 |
| Root | AP0140C01R.1 | 49796 | 20.86 | 25.69 | 26.74 |
| Leaf | AP0140C01L.4 | 49796 | 23.76 | 25.84 | 25.92 |
| Root | AP0140G01R.13 | 49802 | 19.96 | 25.92 | 25.81 |
| Leaf | AP0140C01L.7 | 49796 | 23.34 | 25.93 | 26.78 |
| Root | AP0140B01R.9 | 49794 | 21.02 | 26.11 | 26.53 |
| Root | AP0140G01R.14 | 49802 | 20.29 | 26.32 | 27.1 |
| Root | AP0140G01R.16 | 49802 | 19.8 | 26.38 | 27.53 |
| Root | AP0140G01R.2 | 49802 | 21.88 | 26.4 | 27.52 |
| Leaf | AP0140C01L.2 | 49796 | 22.58 | 26.53 | 27.45 |
| Root | AP0140C01R.10 | 49796 | 21.28 | 26.62 | 28.2 |
| Root | AP0140C01R.6 | 49796 | 21.39 | 26.64 | 28.63 |
| Root | AP0140G01R.11 | 49802 | 20.33 | 26.81 | 27.07 |
| Root | AP0140C01R.2 | 49796 | 22.18 | 26.86 | 28.32 |
| Root | AP0140G01R.6 | 49802 | 20.03 | 27.04 | 28.21 |
| Leaf | AP0140D01L.12 | 49798 | 25.53 | 27.12 | 27.3 |
| Leaf | AP0140D01L.4 | 49798 | 24.37 | 27.21 | 27.88 |
| Root | AP0140G01R.8 | 49802 | 20.02 | 27.25 | 28.7 |
| Leaf | AP0140C01L.12 | 49796 | 24.19 | 27.32 | 27.6 |
| Leaf | AP0140A01L.3 | 49792 | 24.57 | 27.42 | 28.22 |
| Leaf | AP0140C01L.10 | 49796 | 23.26 | 27.43 | 28.36 |
| Leaf | AP0140C01L.3 | 49796 | 24.04 | 27.46 | 27.78 |
| Root | AP0140C01R.12 | 49796 | 24.23 | 27.47 | 28.67 |
| Leaf | AP0140C01L.6 | 49796 | 23.57 | 27.53 | 27.94 |
| Root | AP0140C01R.14 | 49796 | 23.2 | 27.57 | 29.91 |
| Leaf | AP0140C01L.14 | 49796 | 23.06 | 27.62 | 27.99 |
| Leaf | AP0140D01L.3 | 49798 | 23.88 | 27.65 | 27.69 |
| Root | AP0140C01R.4 | 49796 | 23.22 | 27.65 | 29.52 |
| Leaf | AP0140C01L.5 | 49796 | 23.77 | 27.69 | 28.54 |
| Leaf | AP0140C01L.11 | 49796 | 23.94 | 27.69 | 27.9 |
| Leaf | AP0140C01L.13 | 49796 | 23.97 | 27.72 | 28.36 |
| Root | AP0140G01R.9 | 49802 | 20.66 | 27.74 | 28.81 |
| Root | AP0140G01R.15 | 49802 | 21.75 | 27.88 | 29.65 |
| Leaf | AP0140A01L.15 | 49792 | 21.77 | 27.92 | 28.96 |
| Root | AP0140C01R.11 | 49796 | 23.57 | 28.03 | 29.9 |
| Root | AP0140C01R.13 | 49796 | 23.71 | 28.09 | 29.63 |
| Leaf | AP0140G01L.11 | 49802 | 22.86 | 28.23 | 28.5 |
| Root | AP0140C01R.5 | 49796 | 23.78 | 28.3 | 30.44 |
| Leaf | AP0140A01L.2 | 49792 | 23.14 | 28.5 | 29.35 |
| Root | AP0140A01R.15 | 49792 | 20.37 | 28.53 | 29.25 |
| Root | AP0140A01R.7 | 49792 | 21.67 | 28.63 | 28.97 |
| Root | AP0140D01R.2 | 49798 | 21.53 | 28.69 | 30.26 |
| Leaf | AP0140A01L.8 | 49792 | 22.51 | 28.75 | 27.36 |
| Leaf | AP0140D01L.2 | 49798 | 23.61 | 28.76 | 29.87 |
| Root | AP0140G01R.4 | 49802 | 21.62 | 28.89 | 29.57 |
| Leaf | AP0140A01L.11 | 49792 | 24.49 | 29.23 | 29.84 |
| Root | AP0140G01R.3 | 49802 | 21.62 | 29.27 | 29.74 |
| Root | AP0140G01R.12 | 49802 | 23.15 | 29.32 | 29.97 |
| Leaf | AP0140E01L.1 | 49801 | 22.28 | 29.32 | 30.75 |
| Leaf | AP0140G01L.1 | 49802 | 22.94 | 29.33 | 30.38 |
| Leaf | AP0140A01L.7 | 49792 | 22.91 | 29.37 | 29.87 |
| Leaf | AP0140E01L.11 | 49801 | 24.65 | 29.53 | 30.7 |
| Root | AP0140C01R.3 | 49796 | 25.11 | 29.71 | 30.98 |
| Leaf | AP0140A01L.6 | 49792 | 23.33 | 29.82 | 30.81 |
| Leaf | AP0140A01L.5 | 49792 | 24.08 | 29.87 | 31.5 |
| Leaf | AP0140A01L.9 | 49792 | 22.88 | 29.88 | 31.07 |
| Leaf | AP0140A01L.14 | 49792 | 23.92 | 29.89 | 31.05 |
| Root | AP0140A01R.10 | 49792 | 21.64 | 29.92 | 31.59 |
| Root | AP0140A01R.3 | 49792 | 21.36 | 29.93 | 30.5 |
| Root | AP0140A01R.9 | 49792 | 20.74 | 29.97 | 31.25 |

We claim:

1. A method of quantifying the level of expression of a heterologous polynucleotide in a transgenic plant or plant cell, the method comprising the steps of:
   a. isolating nucleic acids from a transgenic plant or plant cell, wherein the transgenic plant or plant cell comprises a heterologous polynucleotide operably linked to a heterologous terminator sequence, wherein the heterologous terminator sequence is a SB-GKAF terminator sequence; and
   b. quantifying the level of expression of the heterologous polynucleotide by real-time reverse transcriptase polymerase chain reaction using a forward primer and a reverse primer, wherein the forward primer and the reverse primer hybridize to the heterologous terminator sequence or the complement thereof.

2. A method of measuring the copy number of a heterologous polynucleotide in a transgenic plant or plant cell, the method comprising the steps of:
   a. isolating nucleic acids from a transgenic plant or plant cell, wherein the transgenic plant or plant cell comprises a heterologous polynucleotide operably linked to a heterologous terminator sequence, wherein the heterologous terminator sequence is a SB-GKAF terminator sequence; and
   b. quantifying the copy number of the heterologous polynucleotide by real-time polymerase chain reaction using a forward primer and a reverse primer, wherein the forward primer and the reverse primer hybridize to the heterologous terminator sequence or the complement thereof.

3. The method of claim 1 wherein the quantification of the level of expression of the heterologous polynucleotide of step (b) is done by real-time reverse transcriptase PCR using a probe that hybridizes to the heterologous terminator sequence or the complement thereof.

4. The method of claim 3, wherein the probe hybridizes to the region of the SB-GKAF terminator sequence bounded by the forward primer and the reverse primer.

5. The method of claim 4, wherein the forward primer comprises SEQ ID NO:2, the reverse primer comprises SEQ ID NO:3 and the probe comprises SEQ ID NO:4.

6. The method of claim 4, wherein the forward primer comprises SEQ ID NO:5, the reverse primer comprises SEQ ID NO:6 and the probe comprises SEQ ID NO:7.

7. The method of claim 3, wherein the transgenic plant or plant cell is a maize plant or plant cell.

8. The method of claim 2 wherein the quantification of the copy number of the heterologous polynucleotide of step (b) is done by real-time PCR using a probe that hybridizes to the heterologous terminator sequence or the complement thereof.

9. The method of claim 8, wherein and the probe hybridizes to the region of the SB-GKAF terminator sequence bounded by the forward primer and the reverse primer.

10. The method of claim 9, wherein the forward primer comprises SEQ ID NO:2, the reverse primer comprises SEQ ID NO:3 and the probe comprises SEQ ID NO:4.

11. The method of claim 9, wherein the forward primer comprises SEQ ID NO:5, the reverse primer comprises SEQ ID NO:6 and the probe comprises SEQ ID NO:7.

12. The method of claim 8, wherein the transgenic plant or plant cell is a maize plant or plant cell.

13. A method of quantifying the level of expression of at least two heterologous polynucleotides present in at least two transgenic plants or plant cells, the method comprising the steps of:
   a. isolating nucleic acids from at least two transgenic plants or plant cells, wherein a first transgenic plant or plant cell comprises a first heterologous polynucleotide operably linked to a heterologous terminator sequence, and wherein a second transgenic plant or plant cell comprises a second heterologous polynucleotide operably linked to the heterologous terminator sequence, wherein the heterologous terminator sequence is a SB-GKAF terminator sequence;
   b. optionally, isolating nucleic acids from additional transgenic plants or plant cells, wherein each of the additional transgenic plants or plant cells comprises an additional heterologous polynucleotide operably linked to the heterologous terminator sequence; and
   c. quantifying the level of expression of the first heterologous polynucleotide, the second heterologous polynucleotide and the optional additional heterologous polynucleotides by real-time reverse transcriptase polymerase chain reaction using a forward primer and a reverse primer, wherein the forward primer and the reverse primer hybridize to the heterologous terminator sequence or the complement thereof.

14. The method of claim 13 wherein the steps of isolation of nucleic acids and quantifying the level of expression of heterologous polynucleotides from additional transgenic plants are done for at least one hundred additional transgenic plants or plant cells.

15. The method of claim 13, wherein the quantifying step uses a probe which hybridizes to the region of the SB-GKAF terminator sequence bounded by the forward primer and the reverse primer.

16. The method of claim 15, wherein the forward primer comprises SEQ ID NO:2, the reverse primer comprises SEQ ID NO:3 and the probe comprises SEQ ID NO:4.

17. The method of claim 15, wherein the forward primer comprises SEQ ID NO:5, the reverse primer comprises SEQ ID NO:6 and the probe comprises SEQ ID NO:7.

18. The method of claim 13, wherein the transgenic plant or plant cell is a maize plant or plant cell.

19. The method of claim 14, wherein the transgenic plant or plant cell is a maize plant or plant cell.

* * * * *